Figure 5:
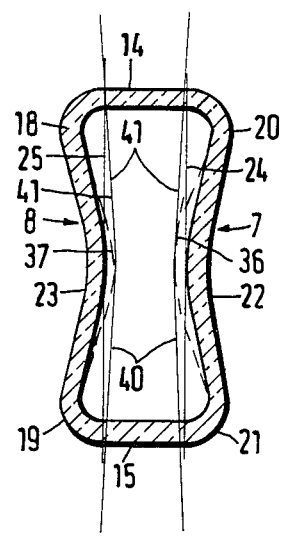

United States Patent [19]

Baldszun et al.

[11] Patent Number: 4,560,269

[45] Date of Patent: Dec. 24, 1985

[54] CELL FOR MIXING OPERATIONS AND FOR OPTICAL EXAMINATION

[75] Inventors: Karl Baldszun, Schenefeld; Thomas Grazianski; Günther Kühn, both of Hamburg, all of Fed. Rep. of Germany

[73] Assignee: Eppendorf Gerätebau Netheler & Hinz GmbH, Hamburg, Fed. Rep. of Germany

[21] Appl. No.: 561,551

[22] Filed: Dec. 14, 1983

[30] Foreign Application Priority Data

Dec. 16, 1982 [DE] Fed. Rep. of Germany ....... 3246592

[51] Int. Cl.[4] ............................................. G01N 21/03
[52] U.S. Cl. .................................. 356/246; 356/427; 356/440
[58] Field of Search ....................... 356/246, 440, 427

[56] References Cited

U.S. PATENT DOCUMENTS

| | | | |
|---|---|---|---|
| 2,927,209 | 3/1960 | Jones et al. | 356/246 |
| 3,263,554 | 8/1966 | Pickels | 356/246 |
| 4,021,124 | 5/1977 | Sarstedt | 356/246 |
| 4,229,104 | 10/1980 | Lahme et al. | 356/440 |
| 4,332,471 | 1/1982 | Gross | 356/246 |

Primary Examiner—John E. Kittle
Attorney, Agent, or Firm—Toren, McGeady, Stanger, Goldberg & Kiel

[57] ABSTRACT

A cell for mixing operations and for optical examinations of liquids has a measuring region which has a small cubic capacity and a relatively large height. In a horizontal cross-section that measuring region has curved transitional wall portions between parallel end wall portions for receiving incident radiation and side walls. In the measuring region, the side walls have inwardly curved portions, which protrude inwardly to such an extent that in a transverse sectional view a tangent to the apex of each inwardly curved portion intersects the parallel end wall portions at an edge thereof or at a point which is inwardly spaced from said edge so that a double-tapered beam of measuring radiation will be closely approached by the inwardly curved side wall portion. At least one side wall portion may constitute a positive lens.

18 Claims, 10 Drawing Figures

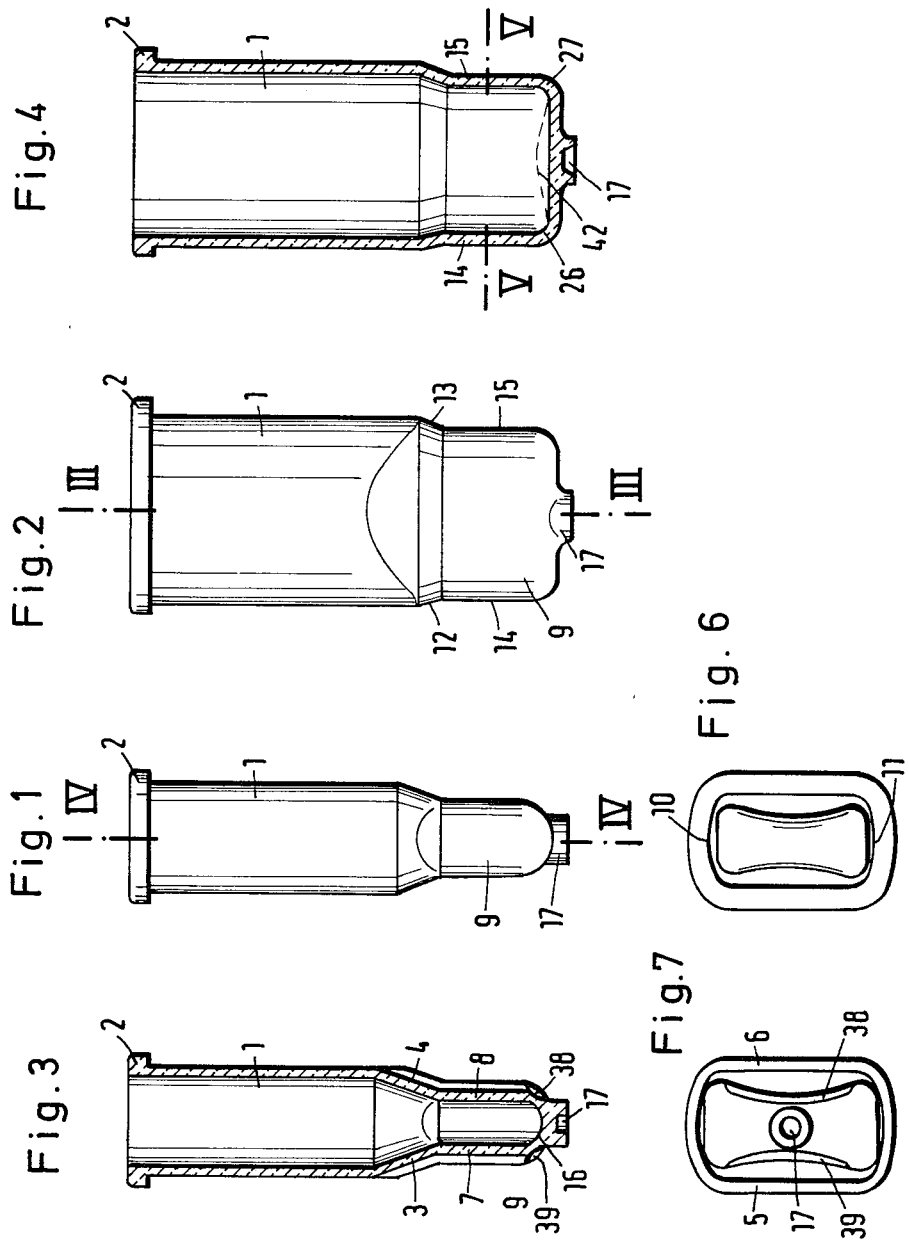

CELL FOR MIXING OPERATIONS AND FOR OPTICAL EXAMINATION

This invention relates to a cell for mixing operations and for an optical examination of liquids, which cell comprises two mutually opposite, parallel end wall portions, which are transparent to radiation, and two mutually opposite side wall portions which together with said end wall portions define a measuring region.

Such cells are known, e.g., from German Patent Publication No. 27 10 889. In the cell disclosed in that publication, the cell cavity includes a measuring region, which is defined by said end wall portions and has an intermediate portion which is enlarged in a direction which is transverse to the direction in which said end wall portions are spaced apart and is defined by side wall portions, which include an obtuse angle with the end wall portions. That design has been adopted to permit a thorough mixing even of a small amount of liquid in the cell. The mutually opposite, parallel end wall portions may be spaced up to about 10 centimeters apart. This applies also to the cell embodying the invention. In this connection it is known to effect a mixing operation in that an oscillating angular movement about the vertical center line of the cell through a predetermined angle is imparted to the cell. It is also known to mix liquids in the cell by a translational movement imparted to the cell so that the center line of the cell is moved to different positions which are parallel to themselves. Both kinds of mixing motions are included for the purposes of the present invention. In connection with the known design it has been believed that it is desirable that the provision of the side walls with outwardly extending surface portions which abut the end wall portions at an obtuse angle permits mixing operations which are more effective than those performed in a space which is rectangular or circular in cross-section. An angular mixing operation in a space which is circular in cross-section will not be effective because the liquid column contained in said space will remain at rest during a rapid oscillation of the circular wall of the cell. In a space which is rectangular in cross-section, the contents of the cell will follow the motion of the cell too closely so that the result of the mixing operation will be unsatisfactory particularly at the corners.

From the above-mentioned publication it is known that the cell may comprise upwardly and outwardly inclined surfaces which define an enlarged space between the narrow measuring region and the upper region of the cell cavity. For that design, transitional wall portions are used, which are defined by oblique junctions, particularly adjacent to the measuring region. Said junctions extend at right angles to the parallel end walls and define enlarged portions of the cell cavity. In that case a larger quantity of liquid will be required and the mixing operation will involve an upwardly directed component of motion. Whereas the known design described in the above-mentioned publication affords substantial advantages over other known designs, it can be improved from the aspects outlined above and from other aspects, also because the known cell is intended for measurements using transmitted light and is less suitable for a measurement using scattered fluorescent light.

For a measurement using scattered fluorescent light, light is projected into the cell through one of the end wall portions and the scattered fluorescent radiation which is thus produced and emitted from the cell approximately at right angles to the incident radiation is measured adjacent to the side walls. In such operation the influence of the incident radiation on the measurement can be eliminated to a large extent.

Laid-open German Application No. 29 22 697 discloses a cell which is intended for optical examinations and has a bottom which is downwardly convexly curved and two planar side walls, which include an oblique angle with each other. The bottom has been described as tub-shaped and the end faces are similar to those described hereinbefore and adjoin the tublike bottom along semicircular lines so that corners are formed. External ribs are provided to permit the cell to be held in a well-like stand, in which the cell proper, particularly its measuring portion, comprises an outwardly and upwardly enlarged region defined by planar walls, which are upwardly and outwardly inclined.

German Patent Specification No. 25 08 527 discloses a cell which has a parallelepipedic cavity, which is joined at its lower end to a tapered cavity by inclined transitional surfaces. The tapered cavity is also defined by mutually opposite wall portions, which are parallel to each other. The tapered cavity accommodates a U-shaped heat-conducting body, which is held between outwardly protruding ribs.

In that cell, the measuring region is also rectangular in cross-section. That configuration is not desirable, particularly because capillary forces occur at the corners.

This invention relates to a cell for mixing operations and for optical examinations. A known cell which is intended only for optical examinations has been provided by Compur in Munich and has side walls which define a constriction. In that known cell the parallel end wall portions for transmitting the incident radiation used for the measurement extend throughout the width of the cell, and straight side wall portions which are inwardly tapered are provided at the ends of said end wall portions and include acute angles with them. In each side wall, said side wall portions terminate at spaced apart locations and are joined by a side wall portion which is also planar. The latter side wall portions of the two side walls are parallel to each other.

Such cell cannot be used for mixing operations. A capillary action results at the corners of the end wall portions for transmitting the incident radiation and the large volume involves a smaller height of the liquid column formed by a given quantity of liquid. That liquid must be mixed before it is placed into the cell because a measuring region having the known cross-section cannot be used for mixing operations and when mixing is attempted, certain ingredients of the liquid will become enriched at the corners, which are spaced a relatively large radial distance from the vertical center line. As a result, no mixing will be effected.

It is an object of the invention to provide a cell which is of the kind described first hereinbefore and which can be used not only for optical examinations but also for mixing operations and which is so improved that the mixing effect produced by the known motions is improved and that relatively small quantities of liquid can be used and additional measurements can be performed through large radiation-transmitting windows.

In accordance with the invention that object is accomplished in that arcuate transitions are provided between the parallel end wall portions and the side walls and the side wall portions defining the measuring region are arcuately inwardly curved and protrude inwardly beyond said arcuate transitions so that in a transverse sectional view a tangent to the apex of each inwardly curved side wall portion intersects each end wall portion at the edge of its planoparallel portion or at a point which is inwardly spaced from said edge to such an extent that in case of a double-tapered beam of measuring radiation transmitted through the cell the inwardly curved wide side wall portions will tangentially approach the throat of said beam of radiation. This design will preclude an occurrence of capillary forces at the corners and owing to the flow lines which are determined by the arcuate transitions also adjacent to the wide side walls will surprisingly result in an effective mixing in the spaces which are enlarged in cross-section near the end wall portions. Particularly during a mixing operation involving an angular motion the inwardly curved portions of the side walls will overcome the inertia of the liquid and will displace the latter so that liquid will flow from one of said end regions to the other.

Particularly in combination with the arcuate transitions between the parallel end wall portions and the wide side walls, the inwardly curved side wall portions will minimize any dead space existing along the path between the parallel end wall portions and the side wall. The inwardly curved portion reduces the volume of the cell cavity at a point at which no measurement by transmitted light is effected. From this aspect the use of a doubletapered beam of measuring radiation is taken into account in that said inwardly curved portions conform optimally to said beam whereas the cell is also suitable for mixing operations.

The inwardly curved portions are generally disposed within the projection of the arcuate transitions in the direction in which light is transmitted along the measuring path so that the quantity of liquid which is required is minimized and the radiation-transmitting windows can be made as large as possible. With that design, the side wall portions will approach the tapered beam of measuring radiation as closely as possible.

The radius of the arcuate transitions between the end wall portions and the side wall portions desirably have a radius of at least 0,5 mm and particularly 0.8 mm in cross-section although said radius may be larger, if desired.

In connection with the above-mentioned cell having a substantially hemicylindrical, downwardly convexly curved bottom, an improvement resides in that thinner wall portions are provided adjacent to the transitions between the mutually oppositely curved side wall portions and the bottom and said thinner wall portions preferably formed with crescent-shaped recesses. The curved and particularly tublike bottom affords the advantage that there are no corners which give rise to capillary forces. At the transitions from the inwardly curved side wall portions to the bottom, the thinner wall portions result in a stress reduction and in an improved heat transfer. Because the thinner wall portions are disposed close to the measuring region, an exact temperature control of the sample will be promoted. The thinner wall portions are preferably formed with external concave recesses adjacent to the transitions between the side walls and the bottom.

According to a preferred feature the bottom has a longitudinally extending, inwardly and upwardly curved portion. That feature can be adopted in conjunction with the features described hereinbefore so that the advantages stated are afforded and the stresses will be decreased.

The above-described design of the side walls of the cell adjacent to the measuring region with inwardly curved portions is a requirement for the provision of at least one side wall as a positive lens, which affords a special advantage in that the measurement of scattered fluorescent light is greatly improved. A great advantage afforded by the invention resides in that the cell can be used for a measurement using transmitted light and for a measurement using scattered light. The inwardly curved portions promote the directing of the energy radiated from the particles as by a positive lens. Such positive lens may be provided on at least one side. For this reason at least one inwardly curved side wall increases in wall thickness toward the center to constitute a concavo-convex lens.

Compared to the design described before, the result for a measurement using scattered fluorescent light will be improved if at least one side wall constitutes a planoconvex positive lens and the side wall of the cell has a planar outside surface. In that case the additional advantage afforded by the inwardly curved side walls will be particularly significant because the outside contour is not interrupted by protruding corners.

From another aspect, one side wall may be curved also outwardly to form a biconvex lens. The provision of the cell with a side wall which constitutes a biconvex lens cannot be adopted in any of the known designs.

In connection with the embodiments described hereinbefore, a feature may be adopted which resides in that each lens is formed on the outside with a cylindrical surface and has a longitudinal axis which is parallel to the vertical center line of the cell. Whereas the positive lens may have approximately in the middle of the height of the measuring region an upwardly and downwardly tapering, arcuate contour so that radiation will also be collected in a vertical plane, a collection in horizontal planes will be more desirable and emitted radiation which has thus been collected can be combined by an external lens system. Particularly in an embodiment having a lens which is parallel to the vertical center line of the cell, a preferred feature resides in that the outside surface of one side wall constitutes a Fresnel lens having a vertical axis. In that case the lens may have a considerable curvature to effect a collection of radiation and this will not involve a greatly protruding wall portion. This design will afford the additional advantage that the vertical segments of the Fresnel lens serve also as heat transfer segments. It will be understood that the inwardly curved portions result in particularly desirable optical conditions and permit a protected arrangement of a lens having a contour which ensures a strong collecting action.

A substantially part-cylindrical convex elevation is suitably provided in the inwardly curved side walls midway between the end wall portions, particularly adjacent to the inwardly curved portion, and said convex elevation may have an axis which is parallel to the vertical center line of the cell. Such outwardly protruding curved portions are also known in conjunction with Fresnel lenses but in that case have only a small radius of curvature. An advantage afforded by the substantially part-cylindrical contour resides in a particularly high focusing power and that the lens portion is provided at a protected location adjacent to the inwardly curved portion.

In the embodiment in which the cell cavity has an upwardly flaring region between the measuring region and the upper portion of the cell and that flaring region is defined by upwardly and outwardly inclined walls, a particularly desirable feature resides in that said inclined walls have hollow conical outside surfaces, which are concavely curved in conformity to the side walls and join the latter along a horizontal junction disposed below said hollow conical surfaces. That design affords the advantage that the distribution of liquid toward the outside will be improved, also as regards the circulation of the mixture, and the above-mentioned junction ensures during a mixing operation that a small quantity of liquid placed into the measuring region will remain in that region. The hollow conical surfaces may also be used to guide the cell in a holder.

Figure 8:
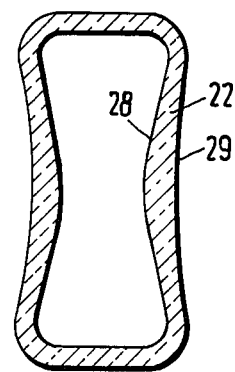
Figure 9:
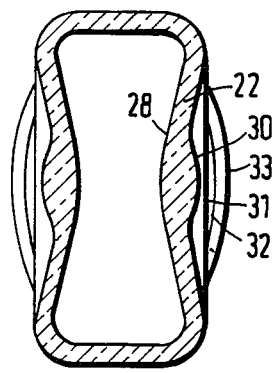
Figure 10:
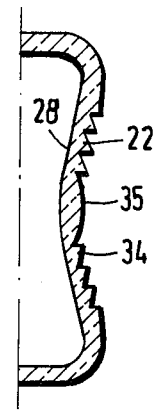

The invention will now be explained with reference to an illustrative embodiment, which is shown on the drawings, in which FIG. 1 is an end elevation showing the cell, FIG. 2 is a side elevation showing the cell, FIG. 3 is a sectional view taken on line III—III in FIG. 2, FIG. 4 is a sectional view taken on line IV—IV in FIG. 1, FIG. 5 is a sectional view taken on line V—V in FIG. 4, FIG. 6 is a top plan view showing the cell of FIG. 1, FIG. 7 is a bottom view of the cell shown in FIG. 3, FIG. 8 is a view that is similar to FIG. 5 and illustrates a side wall which constitutes a system of lenses, FIG. 9 is a view that is similar to FIG. 8 and serves to explain additional features, and FIG. 10 is a view that is similar to FIG. 8 and illustrates a particularly desirable embodiment.

In all Figures, like parts are designated with the same reference characters.

The cell has a narrow upper portion 1, which is elongate in cross-section and which has at its top a peripheral annular flange 2 and in its lower region comprises inclined side wall portions 3, 4, which have concave, hollow conical outside surfaces and constitute transitions from the elongate side wall portions 5, 6 of the upper portion of the cell to the side wall portions 7, 8 defining the measuring region. In the upper portion of the narrow, elongate cell, its end walls have outwardly curved portions 10, 11, which are continued toward the measuring region 9 by small steps 12, 13, with which the end walls extend inwardly to the parallel end wall portions 14, 15, which permit a measurement using transmitted light or using radiation which is incident at right angles to said end wall portions. The cell is closed at its bottom by a downwardly convexly protruding, tublike bottom wall 16, which is provided with a central centering extension 17, which serves to retain the cell in an aligned position in a mixing apparatus.

As is apparent from FIG. 5, the parallel end wall portions 14, 15 are connected to the side wall portions 7, 8 by arcuate transition wall portions 18, 19, 20, 21, which have a radius of an order of at least 0.8 mm, which is large for cells of the present kind. Each of the side wall portions has in its central region an inwardly curved, arcuate portion 22, 23. These inwardly curved portions have such a depth that they are tangent to the lines 24, 25 (FIG. 5) which connect corresponding edges of mutually opposite, parallel end wall portions 14, 15, or the inwardly curved portions 22, 23 may extend beyond said connecting lines as is indicated at 36 and 37 so that the inwardly curved portions of the side wall portions 7, 8 approach a doubletapered beam 40, 41 of measuring radiation as closely as possible.

With this design, the cross-section of the measuring region is defined by curved portions to a substantial extent and is elongate and has no corners. That cross-sectional configuration is suitable for a measurement using very small quantities of liquid and transmitted light and permits a special design of one of the side wall portions 22, 23.

A stressfree transition between the tublike bottom wall 16 and the inwardly curved side wall portions 7, 8 is provided by thinner wall portions 38, 39, which have curved recesses in their outside surfaces. These recesses are substantially crescent-shaped, as is indicated at 38, 39 in FIG. 7. This means that the thinner wall portions have the smallest wall thickness in the regions in which the side wall portions 7, 8 are curved inwardly to the largest extent. That design has also a favorable influence on the heat transfer.

Arcuate transitional wall portions 26, 27 are also provided between the ends of the bottom wall 16 and the parallel end wall portions 14, 15.

For an improved utilization of the volume, the bottom wall 16 may be curved inwardly along the line 42 in FIG. 4.

FIG. 8 is a transverse sectional view which is similar to FIG. 5. The side wall portion 22 has an inside surface 28 and an outside surface 29, which is not parallel to but flatter than the surface 28 so that an effect like that of a positive lens is achieved owing to that design of the side wall portion 22 and to the refractive indices of the cell wall material and of the fluids which adjoin that side wall portion.

In accordance with FIG. 9, that positive lens effect can be improved in that the outside surface has different outwardly convex curvatures in a plurality of steps arranged one over the other. The step 30 is still disposd within the contour of the cell. Another step 31 has a planar outside surface and together with the inside surface 28 constitutes a planoconvex positive lens. Additional steps 32, 33 may be provided, which are curved outwardly to larger extents and form biconvex regions in the side wall portion. The outside surfaces of the outwardly convex steps shown in FIG. 9 are suitably substantially cylindrical surfaces which are centered on a vertical axis, i.e., which are curved about a line that is at right angles to the plane of the drawing.

In the preferred embodiment shown in FIG. 10, the inwardly curved side wall portion 22 is provided on the outside with a Fresnel lens 34, which even in a very small wall thickness produces a particularly strong positive lens effect for radiation from the interior and which provides ribs for improving the heat transfer. In the preferred embodiment said ribs are parallel to the vertical center line of the cell. Midway between the end wall portions, the side wall portion 22 is formed with a substantially part-cylindrical, outwardly convex elevation 35, which has a vertical axis and is disposed within the extent of the inwardly curved portion of the side wall portion 22. Even when the side wall portion does not constitute a Fresnel lens, such elevation 35 will provide a substantial positive lens effect at least in the central portion of the measuring region of the cell.

What is claimed is:

1. In a cell for holding liquids to be mixed or to be subjected to optical examination, which cell comprises a bottom wall and has a cavity defined by and rising from said bottom wall and including a measuring region defined by two mutually opposite, parallel, planar end wall portions adapted to transmit incident radiation into said measuring region, and two mutually opposite side wall portions, the improvement residing in that each of said planar end wall portions is joined to each of said side wall portions by an arcuate transitional wall portion and each of said side wall portions has an inwardly curved portion, which has an apex and protrudes inwardly to such an extent that a horizontal tangent to said apex intersects said planar end wall portions.

2. The improvement set forth in claim 1 as applied to a cell for holding liquids to be subjected to optical examination by a double-tapered beam of radiation which is incident on one of said planar end wall portions and exits through the other of said end wall portions and has a throat between said inwardly curved portions of both said side wall portions, wherein each of said inwardly curved portions protrudes inwardly into close proximity to said beam adjacent to said throat.

3. The improvement set forth in claim 1, wherein each of said inwardly curved portions protrudes inwardly beyond said transitional wall portions associated with the respective side wall portion.

4. The improvement set forth in claim 1, wherein the inside surfaces of said transitional wall portions have a radius of curvature of at least 0.5 mm.

5. The improvement set forth in claim 1, wherein the inside surfaces of said transitional wall portions have a radius of curvature of at least 0.8 mm.

6. The improvement set forth in claim 1, wherein said bottom wall is downwardly convexly curved and constitutes a hemicylinder extending along said side wall portions and said side wall portions and said bottom wall are joined by transitional wall portions which are thinner in part than said side wall portions and said bottom wall.

7. The improvement set forth in claim 6, wherein said thinner transitional wall portions are formed with recesses which are crescent-shaped.

8. The improvement set forth in claim 7, wherein said thinner wall portions are formed with concave recesses on their outside surface.

9. The improvement set forth in claim 6, wherein said bottom wall has an upwardly curved portion which extends in the longitudinal direction of said bottom wall.

10. The improvement set forth in claim 1, wherein at least one of said side wall portions constitutes a positive lens.

11. The improvement set forth in claim 10, wherein at least one of said side wall portions constitutes a concavo-convex lens, which increases in thickness towards its center.

12. The improvement set forth in claim 10, wherein at least one of said side wall portions constitutes a plano-convex positive lens having a planar outside surface on the outside of said side wall portion.

13. The improvement set forth in claim 10, wherein at least one of said side wall portions constitutes a biconvex lens having convex surfaces on the inside and outside of said side wall portion.

14. The improvement set forth in claim 10, wherein said lens has on the outside of said side wall portion a cylindrical surface having a vertical axis.

15. The improvement set forth in claim 10, wherein said lens constitutes a Fresnel lens having a vertical axis.

16. The improvement set forth in claim 10, wherein at least one of said side wall portions is formed on its outside midway between said end wall portions with an outwardly convex, part-cylindrical elevation having a vertical axis.

17. The improvement set forth in claim 16, wherein said part-cylindrical elevation extends only in the inwardly curved portion of said side wall portion.

18. The improvement set forth in claim 1 as applied to a cell in which said side wall portions have concave outside surfaces, said cavity includes above said measuring region an upper region which is larger in cross-section than said measuring region and said side wall portions are adjoined at the top by upwardly and outwardly inclined side wall portions, wherein said inclined side wall portions have upwardly and outwardly inclined, conical, concave outside surfaces and join each of said side wall portions in a horizontal junction below said conical surfaces.

* * * * *